United States Patent
Gupta et al.

(10) Patent No.: US 11,439,400 B2
(45) Date of Patent: Sep. 13, 2022

(54) DELIVERY DEVICE FOR USE WITH AN EMBOLIC MATERIAL

(71) Applicant: BOSTON SCIENTIFIC SCIMED, INC., Maple Grove, MN (US)

(72) Inventors: Ajay Gupta, Shoreview, MN (US); Jeffry D. Johnson, Crystal, MN (US); Nicholas Lee Tassoni, Andover, MN (US); Gary John Pederson, Jr., Albertville, MN (US); Mary-Claire Anderson, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 563 days.

(21) Appl. No.: 16/280,490

(22) Filed: Feb. 20, 2019

(65) Prior Publication Data

US 2019/0262119 A1 Aug. 29, 2019

Related U.S. Application Data

(60) Provisional application No. 62/702,015, filed on Jul. 23, 2018, provisional application No. 62/634,478, filed on Feb. 23, 2018.

(51) Int. Cl.
*A61B 17/12* (2006.01)
*A61F 2/01* (2006.01)
(Continued)

(52) U.S. Cl.
CPC .... *A61B 17/12113* (2013.01); *A61B 17/1215* (2013.01); *A61B 17/12109* (2013.01);
(Continued)

(58) Field of Classification Search
CPC .......... A61B 17/12022; A61B 17/1214; A61B 17/12145; A61B 17/12113; A61B 17/0057; A61B 2017/1205
See application file for complete search history.

(56) References Cited

U.S. PATENT DOCUMENTS

| 5,217,484 A | 6/1993 | Marks |
| 5,261,916 A | 11/1993 | Engelson |
| 5,417,708 A | 5/1995 | Hall et al. |

(Continued)

FOREIGN PATENT DOCUMENTS

| EP | 2146651 A2 | 1/2010 |
| WO | 2008085606 A1 | 7/2008 |
| WO | 2010009019 A1 | 1/2010 |

OTHER PUBLICATIONS

International Search Report and Written Opinion dated May 14, 2019 for International Application No. PCT/US2019/018709.

*Primary Examiner* — Majid Jamialahmadi
(74) *Attorney, Agent, or Firm* — Seager, Tufte & Wickhem LLP

(57) ABSTRACT

Embolic material delivery devices and methods of using them are disclosed. An example embolic material delivery assembly includes an outer member having a lumen extending therein and a distal end region, an inner member disposed within the lumen of the outer member, wherein the inner member includes a first lumen extending therein. The embolic material delivery assembly also includes a first embolic material extending within the first lumen of the inner member, the embolic material having a first distal end region. The embolic material delivery assembly also includes an anchor disposed within the lumen of the outer member, the anchor having a first attachment region. Further, the first distal end region of the first embolic material is coupled to the first attachment region of the anchor.

12 Claims, 15 Drawing Sheets

(51) Int. Cl.
*A61B 90/00* (2016.01)
*A61B 17/00* (2006.01)

(52) U.S. Cl.
CPC .... *A61B 17/12163* (2013.01); *A61B 17/0057* (2013.01); *A61B 17/1214* (2013.01); *A61B 17/12145* (2013.01); *A61B 90/39* (2016.02); *A61B 2017/00867* (2013.01); *A61B 2017/1205* (2013.01); *A61F 2/011* (2020.05); *A61F 2002/018* (2013.01)

(56) References Cited

U.S. PATENT DOCUMENTS

| | | |
|---|---|---|
| 5,639,277 A | 6/1997 | Mariant et al. |
| 5,891,130 A | 4/1999 | Palermo et al. |
| 5,895,391 A | 4/1999 | Farnholtz |
| 5,925,059 A | 7/1999 | Palermo et al. |
| 7,485,122 B2 | 2/2009 | Teoh |
| 8,202,292 B2 | 6/2012 | Kellett |
| 8,328,860 B2 | 12/2012 | Strauss et al. |
| 8,333,796 B2 | 12/2012 | Tompkins et al. |
| 10,238,396 B2 | 3/2019 | Tassoni et al. |
| 2003/0055440 A1 | 3/2003 | Jones et al. |
| 2006/0025801 A1 | 2/2006 | Lulo et al. |
| 2006/0224179 A1* | 10/2006 | Kucharczyk ....... A61B 17/1214 606/200 |
| 2006/0276832 A1 | 12/2006 | Balgobin et al. |
| 2007/0227544 A1 | 10/2007 | Swann et al. |
| 2007/0288049 A1 | 12/2007 | Davis et al. |
| 2016/0228125 A1* | 8/2016 | Pederson, Jr ...... A61B 17/1214 |
| 2018/0028193 A1 | 2/2018 | Mathis et al. |

\* cited by examiner

DELIVERY DEVICE FOR USE WITH AN EMBOLIC MATERIAL

CROSS-REFERENCE TO RELATED APPLICATIONS

This application claims the benefit of priority under 35 U.S.C. § 119 to U.S. Provisional Application Ser. No. 62/634,478, filed Feb. 23, 2018, and U.S. Provisional Application Ser. No. 62/702,015, filed Jul. 23, 2018, the entirety of which is incorporated herein by reference.

BACKGROUND

A wide variety of delivery devices have been developed for medical use including, for example, aiding in the delivery of an embolic material delivery device. These delivery devices are manufactured, packaged, and used according to any one of a variety of different methods. Of the known delivery devices and methods, each has certain advantages and disadvantages. There is an ongoing need to provide alternative delivery devices as well as alternative methods for manufacturing, packaging, and using delivery devices.

BRIEF SUMMARY

The disclosure provides design, material, manufacturing method, packaging, and use alternatives for an embolic material, embolic material delivery devices, and the like. An example embolic material delivery assembly includes an outer member having a lumen extending therein and a distal end region, an inner member disposed within the lumen of the outer member, wherein the inner member includes a first lumen extending therein. The embolic material delivery assembly also includes a first embolic material extending within the first lumen of the inner member, the embolic material having a first distal end region. The embolic material delivery assembly also includes an anchor disposed within the lumen of the outer member, the anchor having a first attachment region. Further, the first distal end region of the first embolic material is coupled to the first attachment region of the anchor.

Alternatively or additionally to any of the embodiments above, wherein the anchor is positioned distal to a distal end of the inner member.

Alternatively or additionally to any of the embodiments above, wherein the anchor includes a coiled wire.

Alternatively or additionally to any of the embodiments above, wherein coupling the first embolic material to the first attachment region of the anchor includes engaging the distal end region of the embolic material with at least one winding of the coiled wire.

Alternatively or additionally to any of the embodiments above, wherein the first embolic material includes a second proximal end region and a length extending between the first distal end region and a second proximal end region, and wherein the proximal end of the embolic material is disposed within the inner member prior to deployment.

Alternatively or additionally to any of the embodiments above, wherein the first embolic material includes a second proximal end region and a length extending between the first distal end region and a second proximal end region, and wherein the second proximal end region extends proximally from the inner catheter prior to deployment.

Alternatively or additionally to any of the embodiments above, wherein the anchor includes an elongated shaft member having a first arcuate portion and a second arcuate portion.

Alternatively or additionally to any of the embodiments above, wherein the attachment region includes an aperture, and wherein coupling the first embolic material to the first attachment region of the anchor includes engaging the aperture.

Alternatively or additionally to any of the embodiments above, wherein the inner member is configured to translate with the lumen of the outer member, and wherein translation of the inner member pushes the coil wire out the distal end of the outer member.

Alternatively or additionally to any of the embodiments above, wherein the inner member includes a second lumen extending therein, and wherein a second embolic material extends within the second lumen of the inner member.

Alternatively or additionally to any of the embodiments above, wherein the anchor member is attached to both the first embolic material and the second embolic material.

Alternatively or additionally to any of the embodiments above, wherein the inner member includes a third lumen, and wherein the anchor is disposed within the third lumen.

Alternatively or additionally to any of the embodiments above, further comprising a deployment shaft disposed within the third lumen, wherein the anchor is positioned distal to a distal end of the deployment shaft.

Alternatively or additionally to any of the embodiments above, wherein the deployment shaft is designed to translate with the third lumen of the inner member, and wherein translation of the deployment shaft pushes the coil wire out the distal end of the outer member.

Another example embolic material delivery assembly includes:

a deployment catheter including a first lumen and a second lumen extending therein;

a first embolic material extending within the first lumen of the inner member, the embolic material having a first distal end region;

a deployment shaft disposed within the second lumen of the inner catheter; and a coil member disposed within the second lumen of the inner catheter, the anchor member having at least a first winding;

wherein the first distal end region of the first embolic material is rigidly engaged with the first winding.

Alternatively or additionally to any of the embodiments above, further comprising an outer catheter including a distal end and a lumen extending therein, and wherein the deployment catheter is disposed within the lumen of the outer catheter.

Alternatively or additionally to any of the embodiments above, wherein the coil member is positioned distal to the deployment shaft.

Alternatively or additionally to any of the embodiments above, wherein the deployment shaft is designed to translate within the second lumen of the deployment catheter, and wherein translation of the deployment shaft pushes the coil member out the distal end of the deployment catheter, the outer catheter or both the deployment catheter and the outer catheter.

Alternatively or additionally to any of the embodiments above, wherein the inner member includes a third lumen extending therein, and wherein a second embolic material extends within the third lumen of the inner member, and wherein the anchor member is attached to both the first embolic material and the second embolic material.

An example method of treating an aneurysm includes:
advancing an embolic material delivery system adjacent an aneurysm, the embolic material delivery system including:
- an outer member having a lumen extending therein and a distal end region;
- an inner member disposed within the lumen of the outer member, wherein the inner member includes a first lumen extending therein;
- a first embolic material extending within the first lumen of the inner member, the embolic material having a first distal end region; and
- an embolic coil disposed within the lumen of the outer member, the embolic coil having a first winding;
- wherein the first distal end region of the first embolic material is rigidly attached to the first winding;

translating the inner catheter relative to the outer catheter, wherein the translation of the inner catheter relative to the outer catheter advances both the embolic coil and the embolic material into the aneurysm.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments of the disclosure in connection with the accompanying drawings, in which.

Figure 1:
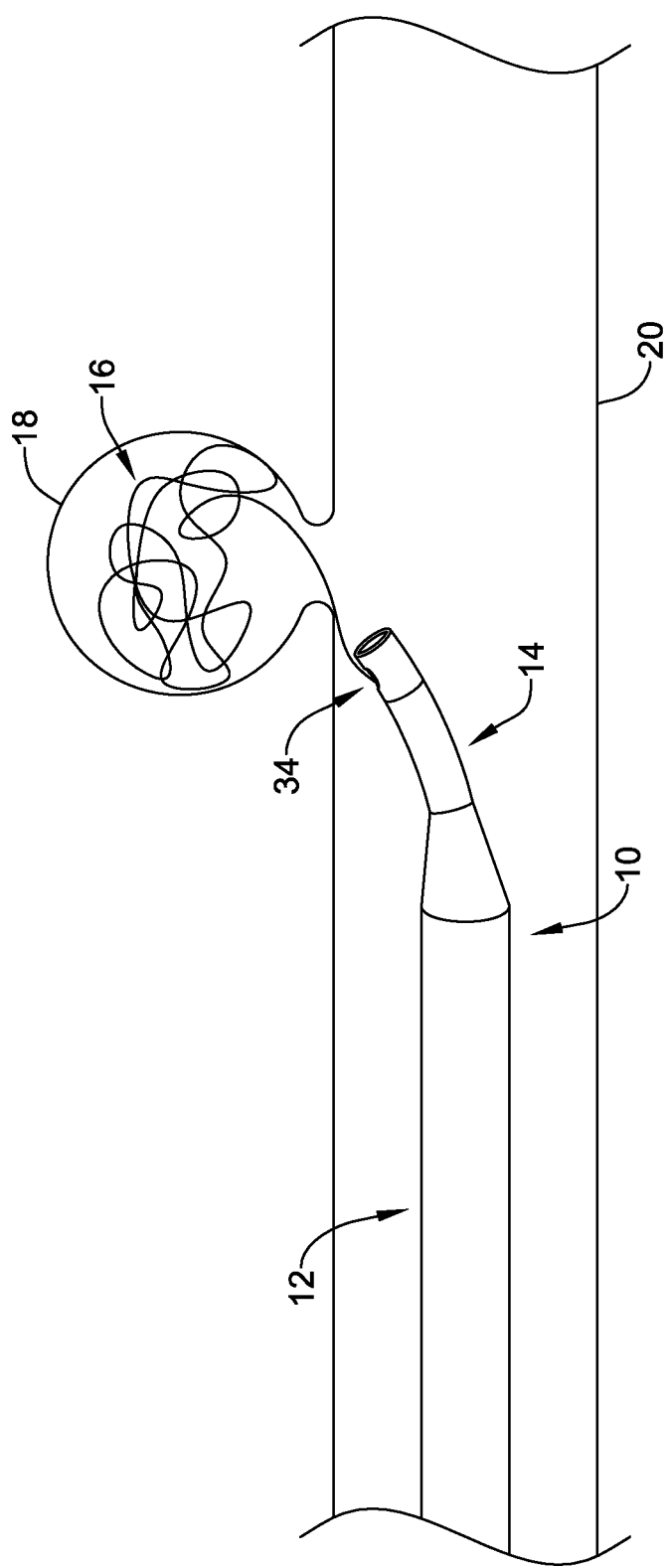
FIG. 1 illustrates an example embolic material delivery device disposed in a blood vessel.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the disclosure. Any feature of any example embodiment may be incorporated into any other embodiment, as appropriate, unless clearly stated to the contrary.

A variety of medical procedures may utilize an embolic material to embolize a target site in the body. For example, a physician may utilize an embolic material to embolize a vessel or aneurysm. Further, in some procedures it may be difficult to predict the correct total volume of embolic material necessary to optimally embolize the target site. Additionally, many mechanical embolics utilized today are only available in predetermined lengths, and therefore, may result in a clinician to overfill (or, alternatively, not adequately fill) a target site. Therefore, it may be desirable to design an embolic material delivery system which permits a clinician to control the amount of embolic material delivered to a target site. Embolic material delivery systems which permit a clinician to control the amount of embolic material delivered to a target site are disclosed.

FIG. 1 shows an example medical device system 10, for example an embolic material delivery system, disposed in a blood vessel 20. The delivery system 10 may include a delivery catheter 12 (e.g., microcatheter) that may be generally configured for advancing within the anatomy of a patient to a position adjacent an area of interest, for example, an aneurysm 18. The delivery catheter 12 may resemble catheters used in the art and they may be sized for the appropriate intervention. As such, it should be understood that there may be a broad range of possible catheter and catheter shaft constructions that may be used. For example, if the delivery catheter 12 is intended to treat the aneurysm 18 in a particular portion of the vasculature, the delivery catheter 12 may be appropriately sized to effectively access that portion of the vasculature.

FIG. 1 further illustrates that the medical delivery system 10 may also include an outer catheter 14. The outer catheter 14 may extend within a lumen of the delivery catheter 12.

Further, the outer catheter 14 may exit a distal end portion of the delivery catheter 12 and extend away from the delivery catheter 12 toward a target site 18. Additionally, the delivery system 10 may also include an embolic material device or other device that may be used to diagnose and/or treat the aneurysm 18. As will be described in greater detail below, the embolic material device may include an embolic material (e.g., multifilament, thrombogenic material, fiber, yarn, string, embolic coil, etc.) 16 that may be placed within the target site (e.g., the aneurysm 18) via the outer catheter 14. For example, FIG. 1 illustrates the embolic material 16 being advanced through an aperture 34 located along the distal end region of the outer catheter 14. In some examples, the embolic material 16 may include a radiopaque material.

Figure 2:
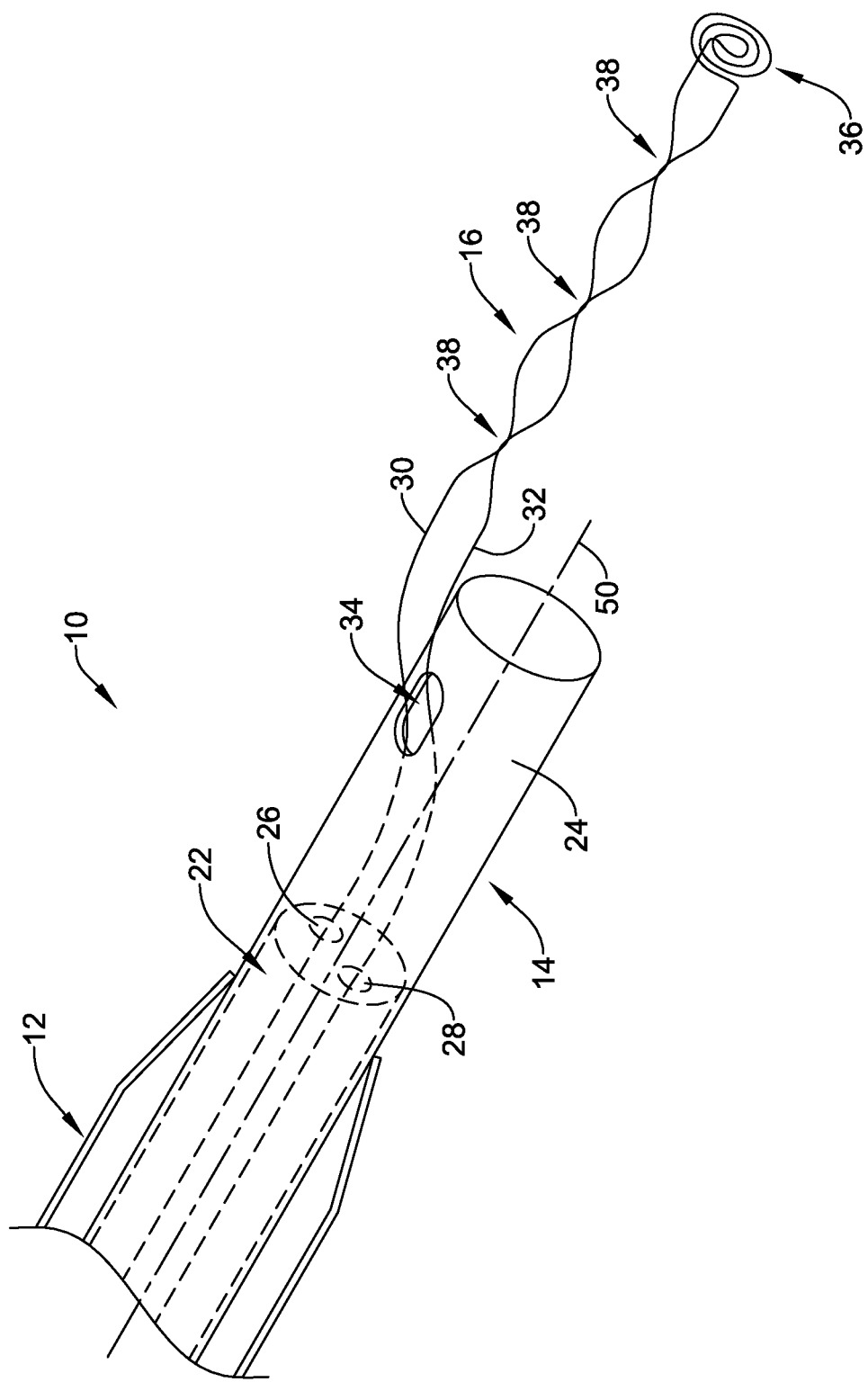
FIG. 2 is a perspective view of an example embolic material delivery device.

FIG. 2 illustrates a distal end region of the delivery system 10 shown in FIG. 1. In particular, FIG. 2 illustrates the distal end region of the outer catheter 14 extending with the lumen of the delivery catheter 12. Additionally, FIG. 2 illustrates that the delivery system 10 may include an inner catheter 22 positioned within a lumen 24 of the outer catheter 14. It can be appreciated that the lumen 24 of the outer catheter 14 may extend from a proximal end region (not shown in FIG. 2) of the outer catheter 14 to a distal end region of the outer catheter 14. As will be described in further detail below, the inner catheter 22 may be configured to shift within the lumen 24 of the outer catheter 14. For example, the inner catheter 22 may be configured to translate along the longitudinal axis 50 of the outer catheter 14. Additionally, it can be appreciated that the inner catheter may be able to rotate within the lumen 24 of the outer catheter 14.

In some instances, the inner catheter 22 may include one or more lumens extending therein. For example, FIG. 2 illustrates the inner catheter 22 including a first lumen 26 and a second lumen 28 extending within the inner catheter 22. The first lumen 26 and the second lumen 28 may be substantially parallel to one another. Further, it can be appreciated that the first lumen 26 and the second lumen 28 of the inner catheter 22 may extend from a proximal end region (not shown in FIG. 2) of the inner catheter 22 to a distal end region of the inner catheter 22. FIG. 2 illustrates that the first lumen 26 and the second lumen 28 may be spaced substantially symmetrically around the longitudinal axis 50 of the inner catheter 22. However, this is not intended to be limiting. It is contemplated that the first lumen 26 and the second lumen 28 may be positioned in a variety of different configurations within the inner catheter 22.

As discussed above, FIG. 2 further illustrates that the delivery system 10 may be utilized to deliver an embolic material to a target site within the body. For example, FIG. 2 illustrates the embolic material 16 (described above with respect to FIG. 1) extending away from the distal end of the outer catheter 14.

It can be appreciated that the embolic material 16 utilized with the medical device delivery system 10 may be designed in a variety of different configurations. For example, FIG. 2 illustrates that the embolic material 16 may include a first embolic material 30 and a second embolic material 32. It can be appreciated that the first embolic material 30 and the second embolic material 32 may be constructed from the same material. However, in other examples the first embolic material 30 and the second embolic material 32 may be constructed from different materials.

In some instances, the embolic material 16 may be initially positioned within a distal portion of the outer catheter 14 and/or the inner catheter 22 prior to being advanced out of the lumen 24 of the outer catheter 14 and placed within a target site (e.g., aneurysm 18). For example, FIG. 2 illustrates that, in some examples, the first embolic material 30 may extend within the the first lumen 26 of the inner catheter 22 and the second embolic material 32 may extend within the second lumen 28 of the inner catheter 22. It can further be appreciated that the first embolic material 30 and the second embolic material 32 may extend from the distal end of the inner catheter 22 to the proximal end of the inner catheter 22. The first embolic material 30 and the second embolic material 32 may be coupled to a hub member or handle (not shown in FIG. 2) which may be positioned adjacent a proximal end of the inner catheter 22.

As discussed above, the embolic material 16 may be initially positioned within a distal portion of the outer catheter 14 and/or the inner catheter 22 while the medical device delivery system 10 is advanced to a target site. After being positioned adjacent the target site (e.g., adjacent the aneurysm 18), the embolic material 16 may be advanced in a proximal-to-distal direction out of both the inner catheter 22 (including the first lumen 26 and the second lumen 28) and the outer catheter 14.

For example, FIG. 2 illustrates that both the first embolic material 30 and the second embolic material 32 may be advanced away from the distal end of the inner catheter 22, through the lumen 24 of the outer catheter and out the aperture 34 (e.g., sidehole) of the outer catheter 14. In some examples, the aperture 34 may extend through a portion or all of the tubular wall of the outer catheter 14. The aperture 34 may extend radially away from the longitudinal axis 50 of the outer catheter 14. It should be noted that while FIG. 2 illustrates the delivery system 10 including two embolic materials (e.g., the first embolic material 30 and the second embolic material 32), it is contemplated that the delivery system 10 may include only a single embolic material or more than two embolic materials. For example, the delivery system 10 may include 1, 2, 3, 4, 5, 6 or more embolic materials.

In some examples, the medical device delivery system 10 may be designed such that advancement of the embolic material 16 (including the first embolic material 30 and the second embolic material 32) in a proximal-to-distal direction may be accomplished by rotating the inner catheter 22 and the outer catheter 14 relative to one another. For example, it is contemplated that the inner catheter 22 may be rotated while the outer catheter 14 is held stationary, or alternatively, the outer catheter 14 may be rotated while the inner catheter 22 is held stationary, wherein either of these mechanisms of action would advance (or retract) the embolic material 16 relative to the distal end of the inner catheter 22. This feature is beneficial because it may permit a clinician to control the specific length and, therefore, volume, of embolic material 16 which is advanced out of the outer catheter 14 and placed within the target site.

Additionally, FIG. 2 illustrates that the delivery system 10 may be designed such that the rotation of the inner catheter 22 and the outer catheter 14 relative to one another may not only advance the embolic material 16 in a proximal-to-distal direction, but it may also cause the first embolic material 30 and the second embolic material 32 to couple (e.g., twist, bunch, etc.) with one another at a plurality of coupling locations 38. For example, FIG. 2 illustrates the first embolic material 30 and the second embolic material 32 positioned substantially parallel to one another (e.g., spaced from one another) after exiting the aperture 34. However, FIG. 2 further illustrates that the first embolic material 30 and the second embolic material 32 may twist (e.g., bunch) with one another at a plurality of coupling locations 38. It can be appreciated that the first embolic material 30 and the second embolic material 32 may be configured such that as the inner catheter 22 is rotated relative to the outer catheter 14, the first embolic material 30 and the second embolic material 32 may advance parallel to one another for a predetermined distance and then again twist together. The embolic material 16 may repeat this process as it is advanced out of the outer catheter 14.

In some instances, the medical device delivery system 10 may include an anchor member attached to the distal end of the embolic material 16. For example, FIG. 2 illustrates the first embolic material 30 and the second embolic material 32 attached to an anchor member 36. The anchor member 36 may include embolic coil, a stent, a plug, or similar structure. It can be appreciated that the anchoring member 36 may be advanced into the target site to provide an anchor prior to the deployment of the embolic material 16 into the target site. Additionally, it can be appreciated that anchoring the distal end of the first embolic material 30 and the second embolic material 32 may encourage the twisting action and creation of the coupling locations 38 as described above. In other words, anchoring the distal ends of the first embolic material 30 and the second embolic material 32 in place may aid the twisting action of the first embolic material 30 with the second embolic material 32.

In some examples, delivering the embolic material 16 may include delivering embolic material of fixed length. For example, in some instances the embolic material 16 delivered by the delivery system 10 may be loaded into the delivery system 10 having already been cut to a predetermined length. In other words, in some instances the embolic material 16 delivered by the delivery system 10 may be loaded into the delivery system 10 as individual, pre-cut, singular pieces of embolic material. These pieces of material may be advanced out of the device via the rotation mechanism described above. Similarly, in other examples, the delivery system 10 may be designed such that a clinician may be able to cut the embolic material 16 at a predetermined length at the proximal end of the device, thereby creating a "customized" length of embolic material 16 which may be advanced out of the device via the rotation methodology described above.

However, in yet other examples, the process of delivering the embolic material 16 to the appropriate portion of the anatomy may include utilizing a cutting mechanism positioned on the distal end region of the delivery system 10 to separate (e.g., detach) the embolic material 16 from the inner catheter 22 and the outer catheter 14. FIGS. 3-6 illustrate an example methodology which utilizes a cutting mechanism positioned on the distal end region of the delivery system 10 for separating the embolic material 16 from the delivery system 10 after a clinician has advanced and positioned a desired amount of embolic material 16 within a target site.

Figure 3:
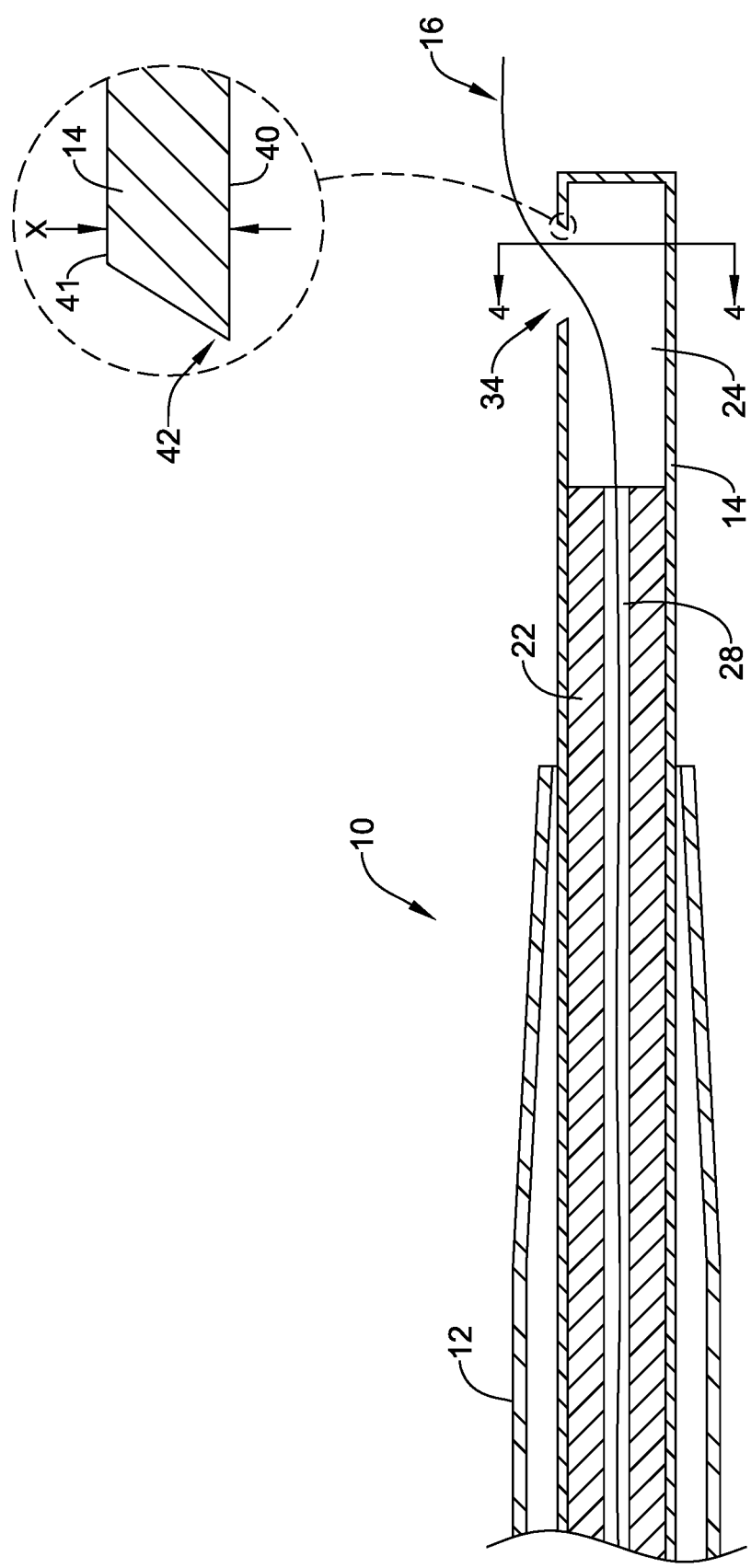
FIG. 3 is a cross-sectional view of the delivery device shown in FIG. 2.

FIG. 3 illustrates a cross-section of the delivery system 10 described with respect to FIG. 2. In particular, FIG. 3 illustrates the outer catheter 14 extending within the lumen of the delivery catheter 12. Further, FIG. 3 illustrates the inner catheter 22 extending within the lumen 24 of the outer catheter 14 and the embolic material 16 extending within the second lumen 28 of the inner catheter 22 (it should be noted that the first lumen 26 is hidden from view in FIG. 3). FIG. 3 further illustrates the embolic material 16 extending within the lumen 24 of the outer catheter 14 and through the aperture 34, whereby it extends distally away from the distal end of the outer catheter 14.

The detailed view of FIG. 3 further illustrates that the outer catheter 14 may include an outer surface 41, an inner surface 40 and a wall extending therebetween. The thickness of the wall of the outer catheter 14 is depicted as "X" in the detailed view of FIG. 3.

Additionally, the detailed view of FIG. 3 illustrates that the aperture 34 may include a cutting edge 42 positioned adjacent to the inner surface 40 of the outer catheter 14. It can be appreciated that the cutting edge 42 may extend circumferentially around the aperture 34. The cutting edge may be described as a sharp, pointed edge which may be created by cutting a bevel in the wall of the outer catheter 14. However, this is not intended to be limiting. It is contemplated that the cutting edge 42 may be created by attaching a circumferential cutting member (e.g., a circumferential blade) to the outer catheter 14 along the aperture 34 adjacent to the inner surface 40 of the outer catheter 14.

Figure 4:
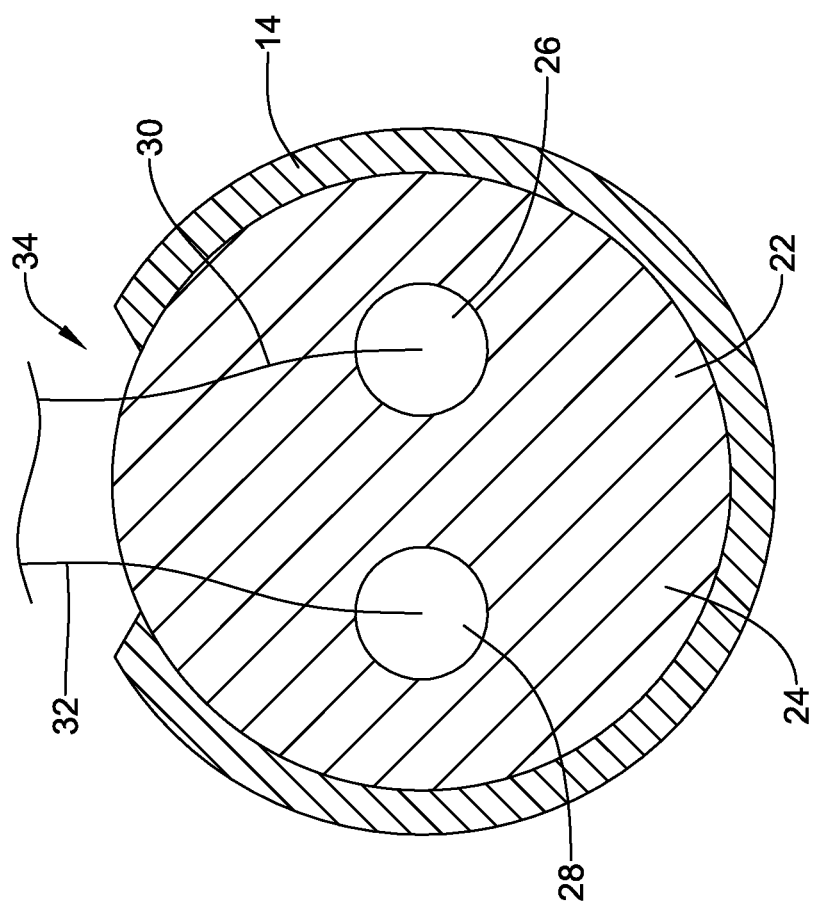
FIG. 4 is a cross-sectional view taken along line 4-4 of the delivery device shown in FIG. 3.

FIG. 4 illustrates a cross-sectional view along line 4-4 of FIG. 3. FIG. 4 shows the inner catheter 22 positioned within the lumen 24 of the outer catheter 14. Additionally, FIG. 4 illustrates both the first embolic material 30 and the second embolic material 32 positioned within the first lumen 26 and the second 28, respectively, of the inner catheter 22. Additionally, FIG. 4 illustrates both the first embolic material 30 and the second embolic material 32 extending through the aperture 34.

Figure 5:
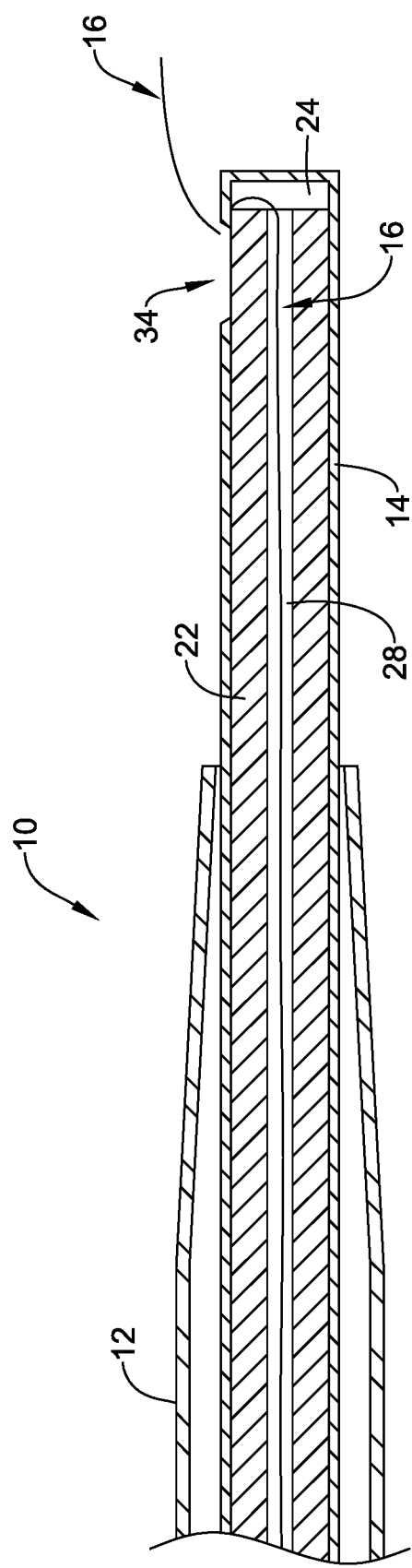
FIG. 5 is a cross-sectional view of another example delivery device.

FIG. 5 illustrates the delivery system 10 described above including the delivery catheter 12, the outer catheter 14 and the inner catheter 22 positioned within the lumen 24 of the outer catheter 14. Additionally, FIG. 5 illustrates the embolic material 16 extending through the second lumen 28 of the inner catheter 22 (it should be noted that the first lumen 26 is hidden from view in FIG. 3). Additionally, FIG. 5 illustrates one example methodology for separating the embolic material 16 from the delivery system 10. In particular, FIG. 5 illustrates that the inner catheter 22 has translated (e.g., shifted) in a proximal-to-distal direction within the lumen 24 of the outer catheter 14. It is noted that the translation of the inner catheter 22 relative to the outer catheter 14 may be controlled by a clinician. Additionally, the inner catheter 22 has shifted to a position in which the distal end of the inner catheter 22 is positioned distal to the aperture 34. Accordingly, this proximal-to-distal translation of the inner catheter 22 may force the embolic material 16 to press against the cutting edge 42 (described with respect to FIG. 3) of the outer catheter 14. In other words, the proximal-to-distal translation of the inner catheter 22 may "cut" (e.g. sever) the embolic material 16 along the cutting edge 42. FIG. 5 illustrates the embolic material 16 after being severed along the cutting edge 42.

Figure 6:
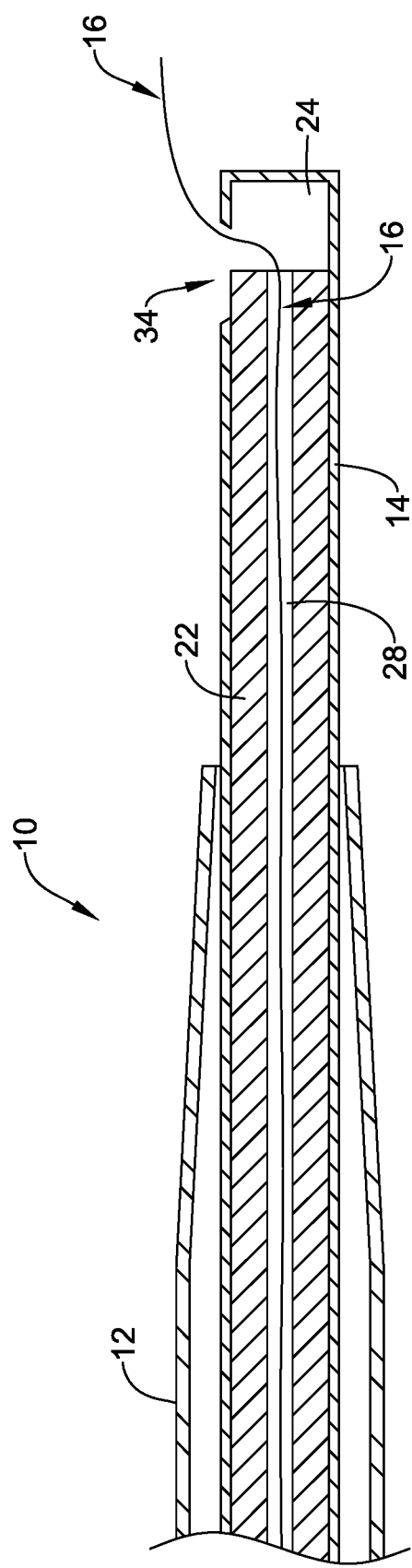
FIG. 6 is a cross-sectional view of another example delivery device.
Figure 7:
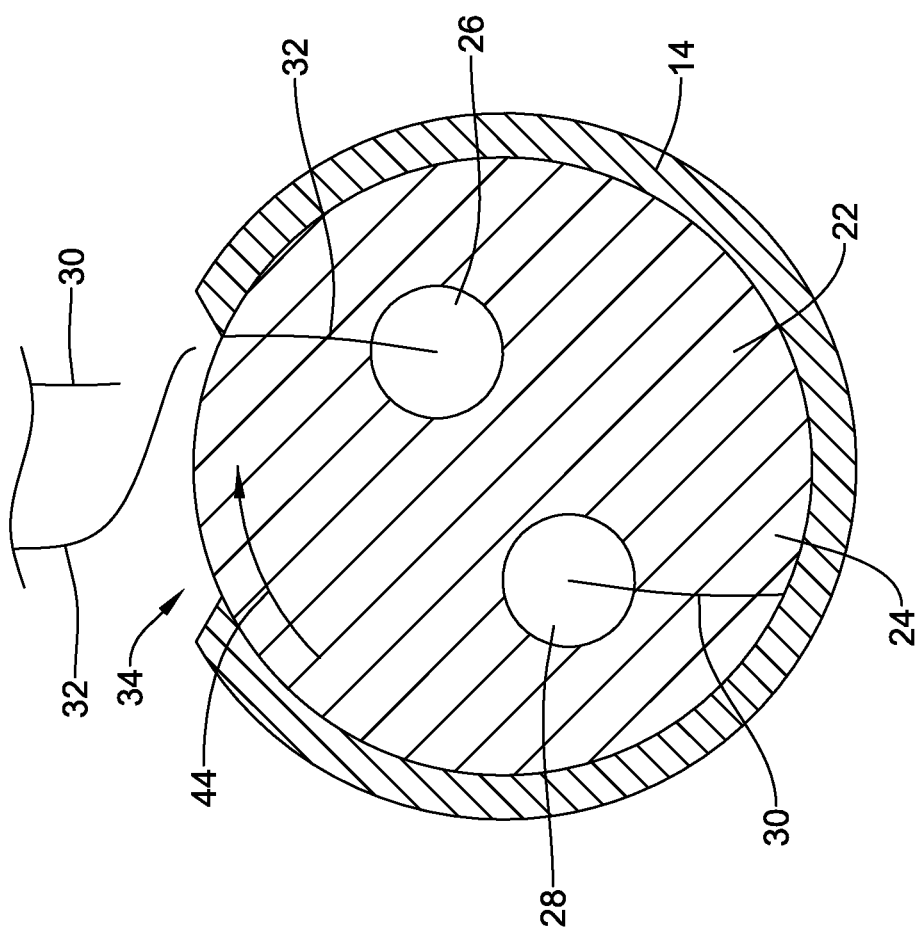
FIG. 7 is a cross-sectional view of another the example delivery device.

FIGS. 6-7 illustrate a second example methodology for separating the first embolic material 30 and the second embolic material 32 from the delivery system 10. FIG. 6 illustrates the delivery system 10 described above including the delivery catheter 12, the outer catheter 14 and the inner catheter 22 positioned within the lumen 24 of the outer catheter 14. Additionally, FIG. 6 illustrates the first embolic material 30 and the second embolic material 32 extending through the first lumen 26 and the second lumen 28, respectively, of the inner catheter 22. Further, FIG. 6 shows inner catheter 22 translated within the lumen 24 of the outer catheter 14 to a position in which the distal end of the inner catheter 22 has advanced distally past the proximal end of the aperture 34 and is thereby aligned positioned within the aperture 34. It is noted that FIG. 6 illustrates the embolic material 16 extending through the aperture 34 prior to being severed. Additionally, the position of the inner catheter 22 relative to the aperture 34 shown in FIG. 6 is designed to sever the embolic material 16. This in contrast with the position of the inner member 22 relative to the aperture 34 shown in FIG. 2 and FIG. 3 (e.g., positioned proximal of the aperture 34), in which the rotation of the inner member 22 advances the embolic material 16 out of the aperture 34.

FIG. 7 illustrates the severing of the embolic material 16 shown in FIG. 6. In particular, FIG. 7 illustrates the inner catheter 22 rotating (depicted by the curved arrow 44) with respect to the outer catheter 14 within the lumen 24 of the outer catheter 14. It is noted that the rotation of the inner catheter 22 relative to the outer catheter 14 may be controlled by a clinician. It is further noted that while FIG. 7 illustrates the inner catheter 22 rotating while the outer catheter remains stationary, it is contemplated that the same effect may be achieved by rotating the outer catheter 14 while the inner catheter 22 is held stationary. Accordingly, the rotation of the inner catheter 22 and the outer catheter 14 relative to one another may force the first embolic material 30 and the second embolic material 32 to press against the cutting edge 42 (described with respect to FIG. 3) of the outer catheter 14. In other words, the rotation of the inner catheter 22 with respect to the outer catheter 14 may "cut" (e.g. sever) each of the first embolic material 30 and the second embolic material 32 along the cutting edge 42. FIG. 7 illustrates the first embolic material 30 and the second embolic material 32 after each has been severed along the cutting edge 42.

Figure 8:
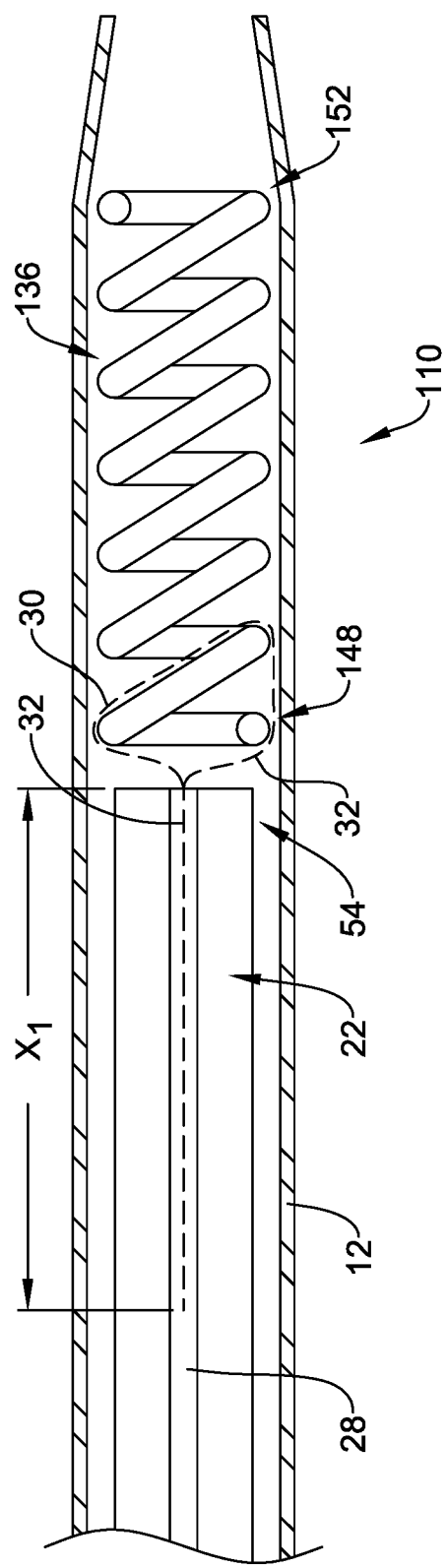
FIG. 8 is a cross-sectional view of another example delivery device.

FIG. 8 illustrates another example medical device delivery system 110. The medical device delivery system 110 may be similar in form and function to other delivery systems described herein. For example, the delivery system 110 may include the inner catheter 22 (described above) positioned within the lumen of the delivery catheter 12 (described above). Additionally, FIG. 8 further illustrates that the medical device system 110 may include the second embolic material 32 extending within the second lumen 28 of the inner catheter 22. As described above, in some examples the second embolic material 32 may include a fixed length "$X_1$" extending with the lumen 28 of the inner catheter 22.

FIG. 8 further illustrates the medical device delivery system 110 may include an anchor 136 positioned distal to a distal end 54 of the inner catheter 22. In at least some embodiments, the anchor member 136 may include an embolic coil 136 having a proximal end region 148, a distal end region 152 and a plurality of windings extending therebetween. Further, the embolic coil 136 may include a variety of different designs and/or configurations. For example, embolic coil 136 may be about 1 to about 100 cm in length and it may have a sufficient flexibility such that embolic coil 136 may be capable of deforming and folding and/or bending within a vascular cavity such as aneurysm. The embolic coil 136 may be pliable and its overall shape may be easily deformed. For example, when inserted into the delivery catheter 12, the embolic coil 136 may be easily straightened to lie axially within the lumen of the delivery catheter 12. Once disposed outside of or advanced out from the distal tip of the delivery catheter 12, the embolic coil 136 may convert into a shapelier, nonlinear form such as shown in FIG. 1, and may be loosely deformed to the interior shape of a vascular cavity. The embolic coil 136 may be formed of any suitable material including any of those listed herein. Additionally, the embolic coil 136, or a portion thereof, may be coated with a thrombogenic agent, a drug or medication, a biological agent, and the like, or any other suitable coating.

FIG. 8 further illustrates that in some examples a proximal portion 148 of the embolic coil 136 may be coupled to the first embolic material 30 (extending within the inner catheter 22 as described above) and/or the second embolic material 32. For example, FIG. 8 illustrates that in some examples the first embolic material 30 and/or the second embolic material 32 may be rigidly secured to the proximal end region 148 of the embolic coil 136. FIG. 8 illustrates that the first embolic material 30 and/or the second embolic material 32 may be secured (e.g., tied, wrapped, wound, etc.) to one or more windings of the embolic coil 136. However, this is not intended to be limiting. Rather, it is contemplated that the first embolic material 30 and/or the second embolic material 32 may be secured to the embolic coil 136 in a variety of configurations. For example, the first embolic material 30 and/or the second embolic material 32 may be welded, soldered, glued, woven, etc. to the embolic coil 136.

While not illustrated in FIG. 8, in some instances it may be desirable to load, in combination, the inner catheter 22 and the embolic coil 136 into the lumen of the delivery catheter 12. In some examples, this may be accomplished by loading the inner catheter 22 and the embolic coil 136 into a separate sheath (not shown in FIG. 8) which is inserted into the lumen of the delivery catheter 12. The separated sheath may then be removed whereby the inner catheter 22 and the embolic coil 136 remain in the lumen of the delivery catheter 12.

Figure 9:
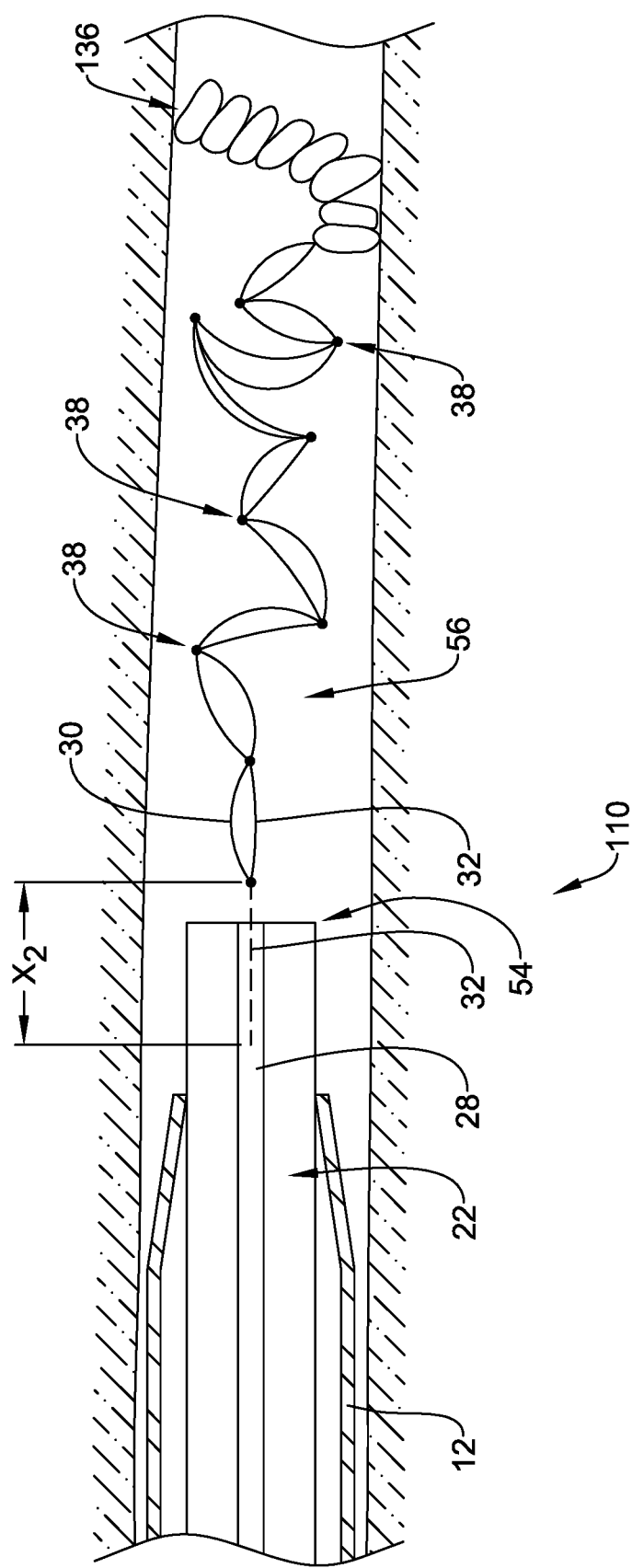
FIG. 9 illustrates the deployment of an embolic material in a body lumen using the example delivery device shown in FIG. 8.

FIG. 9 illustrates the deployment of the embolic coil 136 and the first embolic material 30 and the second embolic material 32 into a body lumen 56. As illustrated in FIG. 9, the inner catheter 22 may be designed such that it can translate in a proximal-to-distal direction within the lumen of the delivery catheter 12. It can be appreciated that translating the inner catheter 22 with the lumen of the delivery catheter may permit the distal end region 54 of the inner catheter 22 to push the embolic coil 136 out of the lumen of the delivery catheter 12 and into the body lumen 56. For example, FIG. 9 illustrates the embolic coil 136 deployed within the body lumen 56 after being pushed out of the distal end of the delivery catheter 12. FIG. 9 further illustrates that the embolic coil has shifted from a substantially linear configuration (shown in FIG. 8) to a nonlinear shape.

Furthermore, as the embolic coil 136 is deployed from the delivery catheter 12, it can be appreciated that the first embolic material 30 and the second embolic material 32 may be "pulled" from within the lumen (e.g., lumen 28) of the inner catheter by the embolic coil 136. As the embolic material 30, 32 leaves the inner catheter 22, it can be appreciated that it may twist and form one or more of the coupling locations 38 as described above.

Figure 10:
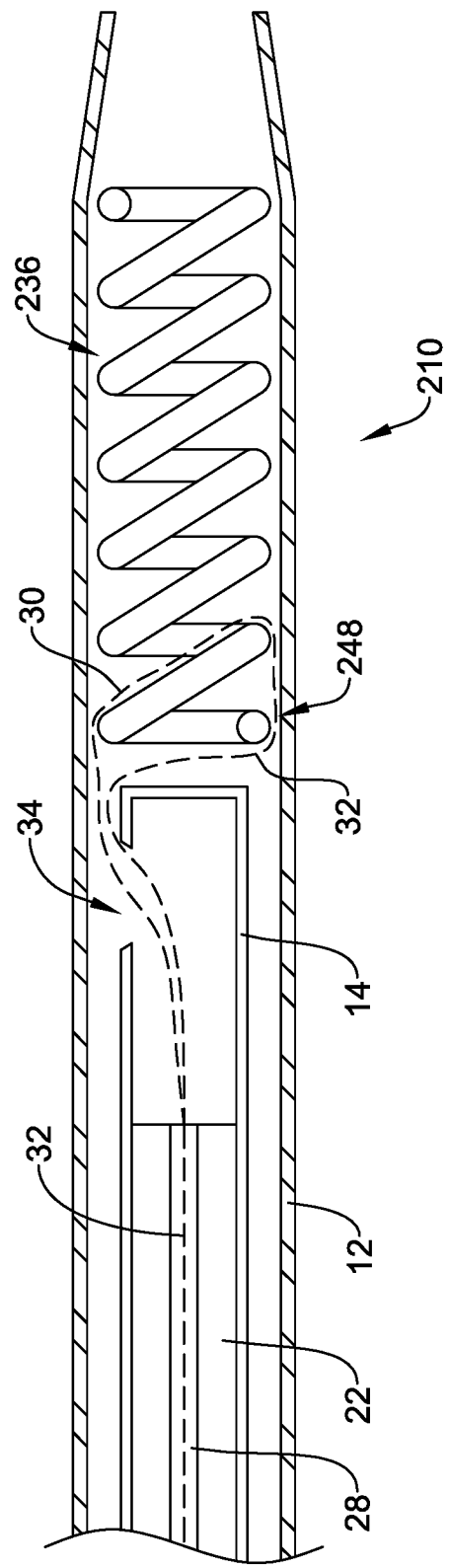
FIG. 10 is a cross-sectional view of another example delivery device.

FIG. 10 illustrates another example medical device delivery system 210. The medical device delivery system 210 may be similar in form and function to other delivery systems described herein. For example, the delivery system 210 may include the inner catheter 22 (described above) positioned within the lumen of the outer catheter 14 (described above), whereby both the inner catheter 22 and the outer catheter 14 are positioned within the lumen of the delivery catheter 12 (described above). It can be appreciated that the relationship of the inner catheter 22, the outer catheter 14 and the delivery catheter 12 may be substantially similar to the delivery system 10 described with respect to FIG. 3.

FIG. 10 further illustrates that the medical device system 210 may include the second embolic material 32 extending within the second lumen 28 of the inner catheter 22. Additionally, as described above, FIG. 10 illustrates that the embolic material 30, 32 may extend through the aperture 34 of the outer catheter and secure to the distal end region 248 of an embolic coil 236 as described above with respect to FIGS. 8-9. For example, proximal portion 248 of the embolic coil 236 may be coupled to the first embolic material 30 (extending within the inner catheter 22 as described above) and/or the second embolic material 32. For example, FIG. 10 illustrates that in some examples the first embolic material 30 and/or the second embolic material 32 may be rigidly secured to the proximal end region 248 of the embolic coil 136. FIG. 10 illustrates that the first embolic material 30 and/or the second embolic material 32 may be secured (e.g., tied, wrapped, wound, etc.) to one or more windings of the embolic coil 236. However, this is not intended to be limiting. Rather, it is contemplated that the first embolic material 30 and/or the second embolic material 32 may be secured to the embolic coil 236 in a variety of configurations. For example, the first embolic material 30 and/or the second embolic material 32 may be welded, soldered, glued, woven, etc. to the embolic coil 236.

Additionally, while it is not shown in the figures, it can be appreciated that the embolic coil 236 may be deployed into a body lumen according to the same methodology as described with respect to the delivery system 110 illustrated in FIG. 9. However, it can further be appreciated that the first embolic material 30 and/or the second embolic material 32 may be fed from a location outside the body, whereby the first embolic material 30 and/or the second embolic material 32 may be severed by the cooperative action/movement of the inner catheter 22 and the outer catheter as described above.

Figure 11:
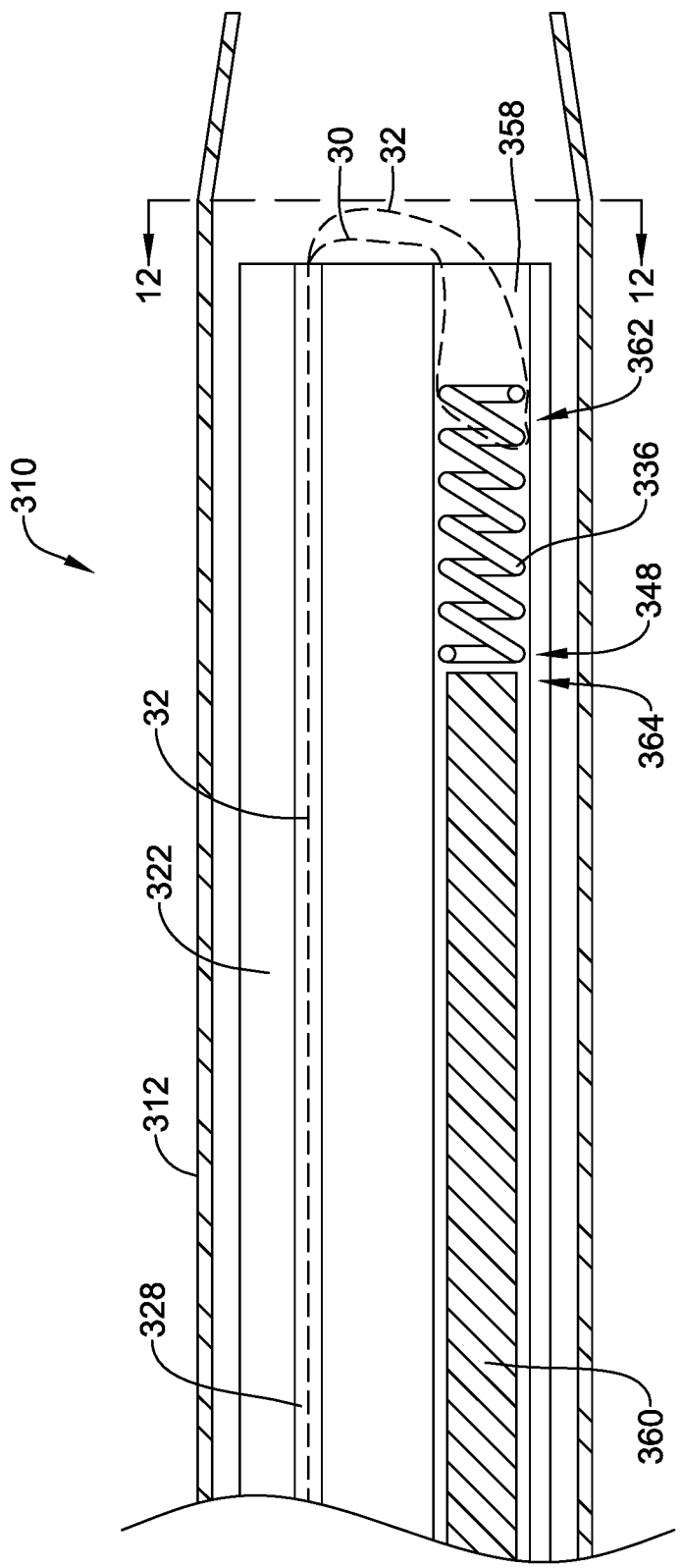
FIG. 11 is a cross-sectional view of another example delivery device.

FIG. 11 illustrates another example medical device delivery system 310. The medical device delivery system 310 may be similar in form and function to other medical device delivery systems described herein. For example, the delivery system 310 may include an inner catheter 322 positioned within the lumen of a delivery catheter 312. Additionally, the inner catheter may include one or more lumens which are designed to permit an embolic material to be positioned therein. For example, FIG. 11 illustrates lumen 328 and the second embolic material 32 extending therein. Additional lumens which permit the first embolic material 30 to pass therein are illustrated in FIG. 12.

Additionally, FIG. 11 illustrates that the inner catheter 322 may include an additional lumen 358 extending therewithin. The lumen 358 may include an actuation rod (e.g., push rod) positioned proximal to an anchor 336 (e.g., embolic coil 336). The embolic coil 336 may have a proximal end region 348, a distal end region 362 and a plurality of windings extending therebetween. As illustrated in FIG. 11, a distal end region 364 of the push rod 360 may be positioned adjacent to the proximal end region 348 of the embolic coil 336.

FIG. 11 further illustrates that distal portion 362 of the embolic coil 336 may be coupled to the first embolic material 30 (extending within the inner catheter 322 as described above) and/or the second embolic material 32. For example, FIG. 11 illustrates that in some examples the first embolic material 30 and/or the second embolic material 32 may be rigidly secured to the distal end region 362 of the embolic coil 336. For example, the first embolic material 30 and/or the second embolic material 32 may extend out of the lumen 328 of the inner catheter 322 and extend into the lumen 358 of the inner catheter 322, whereby the first embolic material 30 and/or the second embolic material 32 may attach to the distal end region 362 of the embolic coil 336. FIG. 10 further illustrates that the first embolic material 30 and/or the second embolic material 32 may be secured (e.g., tied, wrapped, wound, etc.) to one or more windings of the embolic coil 336. However, this is not intended to be limiting. Rather, it is contemplated that the first embolic material 30 and/or the second embolic material 32 may be secured to the embolic coil 336 in a variety of configurations. For example, the first embolic material 30 and/or the second embolic material 32 may be welded, soldered, glued, woven, etc. to the embolic coil 336.

Figure 12:
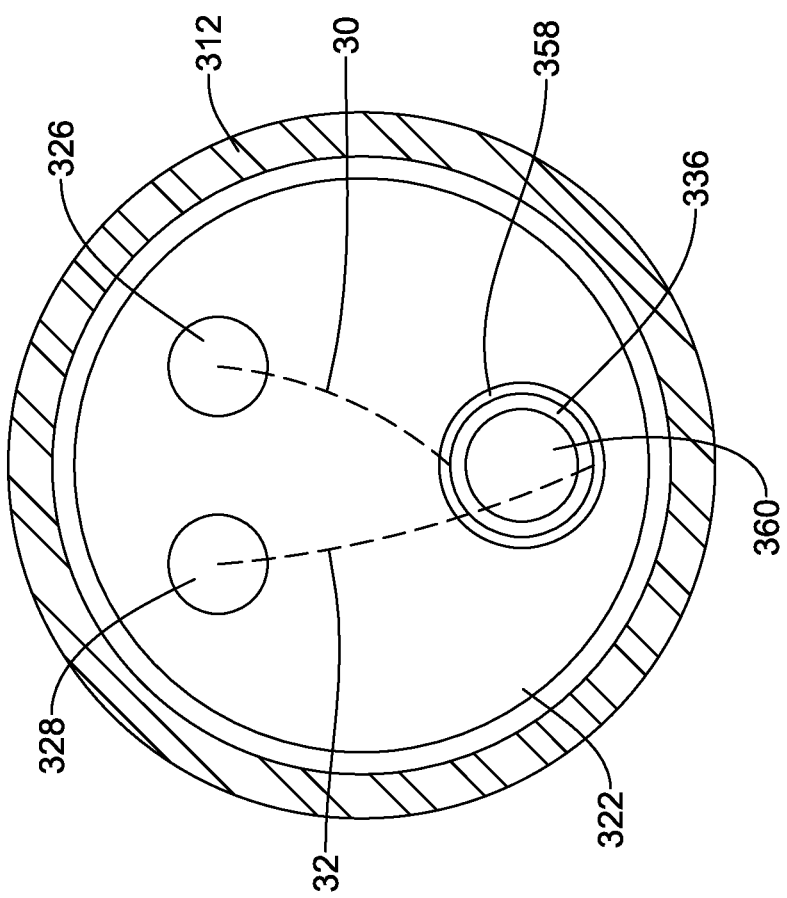
FIG. 12 is an end view of the example delivery device shown in FIG. 11.

FIG. 12 illustrates an end view of the delivery system 310 taken along line 12-12 of FIG. 11. FIG. 12 further illustrates the inner catheter 322 positioned within the lumen of the delivery catheter 312. Additionally, FIG. 12 illustrates the first embolic material 30 extending out of the first lumen 326 of inner catheter 322 and the second embolic material 32 extending out of the second lumen 328 of the inner catheter 322. Further, as described above, FIG. 12 illustrates each of the first embolic material 30 and the second embolic material 32 extending into and attaching to the embolic coil 336 positioned within the lumen 358. Further, FIG. 12 illustrates the push rod 360 radially aligned with the embolic coil 336 within the lumen 358.

Figure 13:
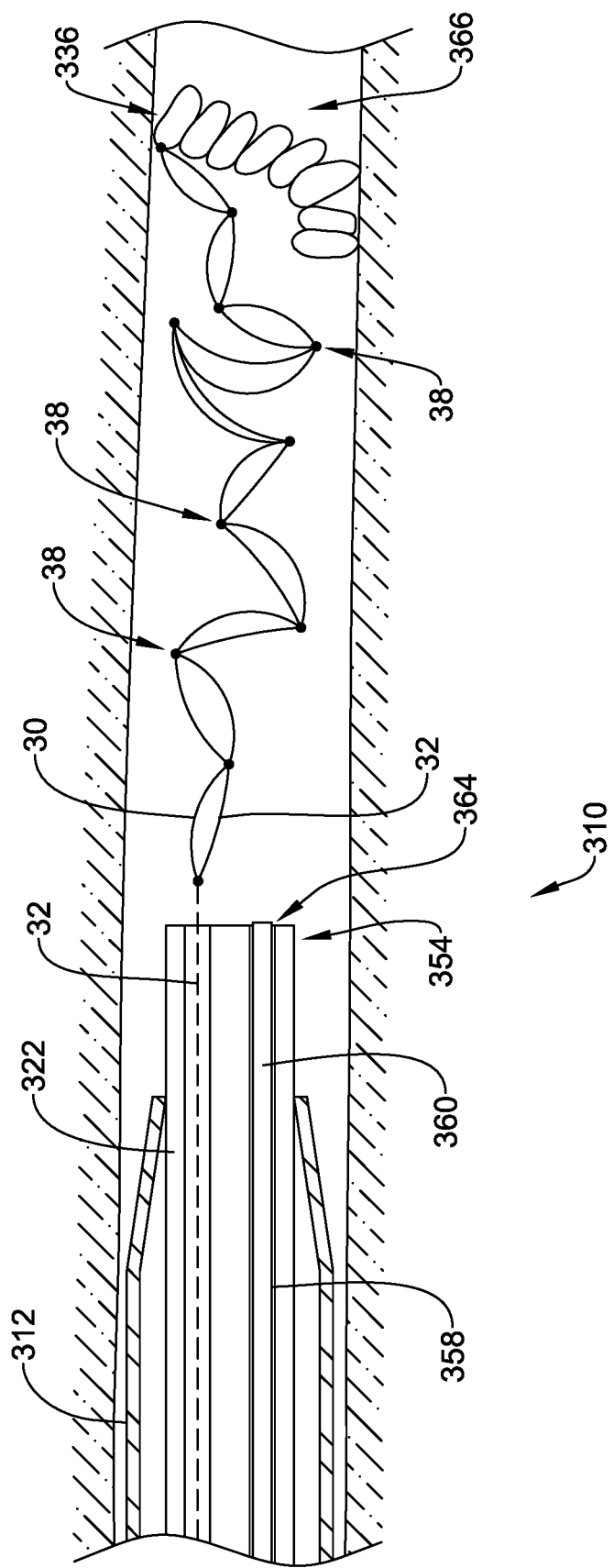
FIG. 13 illustrates the deployment of an embolic material in a body lumen using the example delivery device shown in FIG. 11.

FIG. 13 illustrates the deployment of the embolic coil 336 and the first embolic material 30 and the second embolic material 32 into a body lumen 366. As illustrated in FIG. 13, the inner catheter 322 may be designed such that it may translate in a proximal-to-distal direction within the lumen of the delivery catheter 312. For example, FIG. 13 illustrates the inner catheter 322 has been translated such that it extends out of the distal end of the delivery catheter 312.

Further, the push rod 360 may be designed such that it may translate in a proximal-to-distal direction within the lumen 358 of the inner catheter 322. For example, FIG. 13 illustrates that the push rod 360 has been translated in a proximal-to-distal direction such that it extends to the distal end 354 of the inner catheter 322. It can be appreciated that translating the push rod 360 within the lumen 358 of the inner catheter 322 may permit the distal end region 364 of the push rod 360 to push the embolic coil 336 out of the lumen 358 of the inner catheter 322 and into the body lumen 366. For example, FIG. 13 illustrates the embolic coil 336 deployed within the body lumen 366 after being pushed out of the lumen 358 of the inner catheter 322. FIG. 13 further illustrates that the embolic coil 336 has shifted from a substantially linear configuration (shown in FIG. 11) to a nonlinear shape.

Furthermore, as the embolic coil 336 is deployed from the inner catheter 322, it can be appreciated that the first embolic material 30 and the second embolic material 32 may be "pulled" from within the lumens 26, 28 of the inner catheter by the embolic coil 336. As the embolic material 30, 32 leaves (e.g., is pushed out of) the inner catheter 322, it can be appreciated that it may twist and form one or more of the coupling locations 38 as described above.

Figure 14:
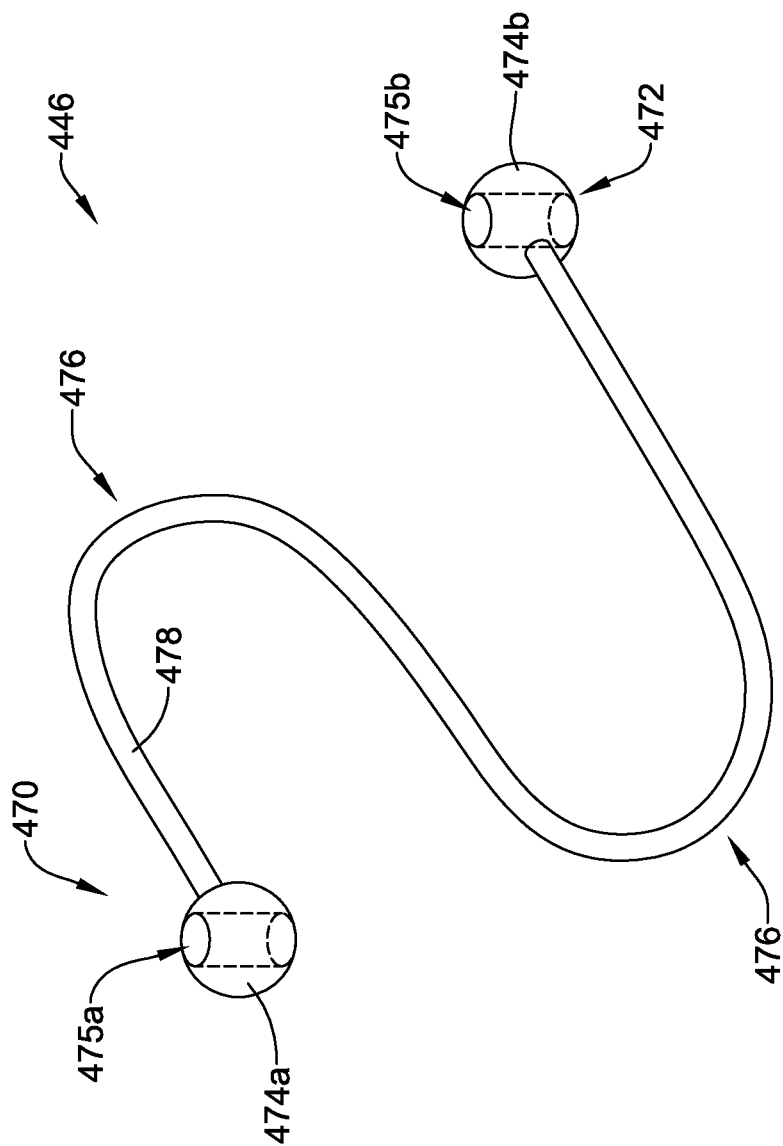
FIG. 14 illustrates an example anchoring device.

FIG. 14 illustrates another example anchor member 446. The anchor member 446 may include a first end region 470, a second end region 472 and a body portion 478 extending therebetween. It can be appreciated that the body portion 478 illustrated in FIG. 14 may be multi-planar. In other words, one or more portions of the body portion 478 may extend away from the plane of the page showing FIG. 14.

The body portion 478 include an elongate member. In some instances, the elongate body portion 476 may be a solid elongate member, while in other instances the elongate body portion 476 may be an elongate tubular member. FIG. 14 further illustrates that the anchor member 446 may include one or more arcuate portions 476. The arcuate portions 476 may permit the anchor member 446 to shift from a first collapsed configuration to a second expanded configuration.

FIG. 14 further illustrates that the anchor member 446 may include a first attachment member 474a positioned adjacent the first end region 470 and a second attachment member 474b positioned adjacent the second end region 472. In some examples, each of the first attachment member 474a and the second attachment member 474b may include a spherical shaped portion. However, this is not intended to be limiting. Rather, the first attachment member 474a and/or the second attachment member 474b may include a variety of different shaped members (e.g., eyelets and/or cylindrical, square, ovular, triangular, rectangular, polygonal-shaped members).

Additionally, each of the first attachment member 474a and the second attachment member 474b may include a first attachment aperture 475a and a second attachment aperture 475b extending through each of the first attachment member 474a and the second attachment member 474b, respectively. As will be described with respect to FIG. 15, the attachment apertures 475a, 475b may be utilized to couple the anchor member 446 to one or more components of a medical device delivery system.

Figure 15:
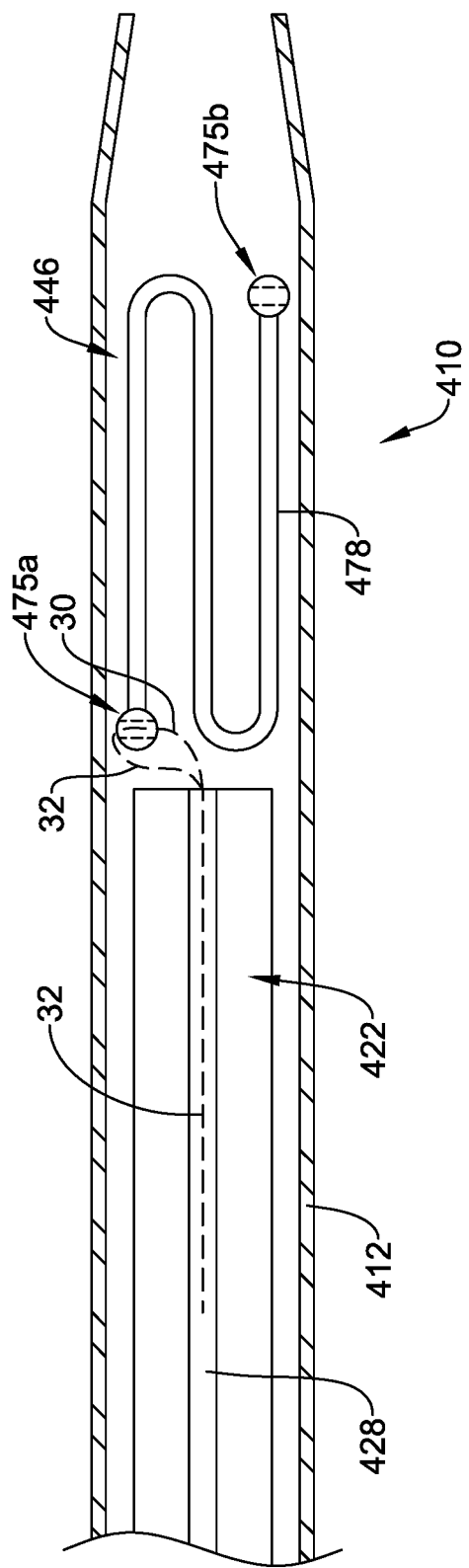
FIG. 15 is a cross-sectional view of another example delivery device.

FIG. 15 illustrates another example medical device delivery system 410. The delivery system 410 may be similar in form and function to other delivery systems described herein. For example, the delivery system 410 may include an inner catheter 422 positioned within the lumen of a delivery catheter 412. Additionally, the inner catheter 422 may include one or more lumens which are designed to permit an embolic material to be positioned therein. For example, FIG. 15 illustrates lumen 428 and the second embolic material 32 extending therein. It can be appreciated that additional lumens which permit the first embolic material 30 to pass within the inner catheter 422 are contemplated.

FIG. 15 further illustrates the anchor member 446 positioned within the lumen of the delivery catheter 412. Specifically, FIG. 15 illustrates the body 478 of anchor member 446 in a collapsed configuration. Additionally, as described above, FIG. 15 illustrates the first embolic material 30 and/or the second embolic material 32 engaged with the aperture 475a of the anchor member 446. In the example shown, the second aperture 475b is free of embolic material. However, it is contemplated that in some examples, the first embolic material 30 and/or the second embolic material 32 may be engaged with the aperture 475a, the aperture 475b or both the first aperture 475a and the second aperture 475b.

While not shown in the figures, it can be appreciated that the anchor member 446 may be deployed from the deployment catheter 412 in a similar manner as that described with respect to FIG. 8 and FIG. 9 above. Further, it can be appreciated that as the inner catheter pushes the anchor 446 out of the distal end of the delivery catheter 412, the anchor 446 may pull the first embolic material 30 and/or the second embolic material 32 out of the inner catheter. Additionally, it can be appreciated that when the anchor member 446 is pushed out of the lumen of the delivery catheter 412, the anchor member 446 may shift from the collapsed configuration shown in FIG. 15 to an expanded configuration designed to anchor within the body.

The materials that can be used for the various components of system 10 (and/or other assemblies or components thereof) and the delivery devices disclosed herein may include those commonly associated with medical devices. For simplicity purposes, the following discussion makes reference to delivery system 10. However, this is not intended to limit the disclosure as the discussion may be applied to other structures or components of system 10 and/or any other suitable devices disclosed herein.

One or more of the components of medical device delivery system 10 may be made from a metal, metal alloy, polymer (some examples of which are disclosed below), a metal-polymer composite, ceramics, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120°

C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, one or more of the components of the medical device delivery system 10 may also be doped with, made of, or otherwise include a radiopaque material. Radiopaque materials are understood to be materials capable of producing a relatively bright image (e.g., and/or otherwise a contrasted image) on a fluoroscopy screen or another imaging technique during a medical procedure. This relatively bright image aids the user of system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of system 10 to achieve the same result.

In some embodiments, a degree of MRI compatibility is imparted into system 10. For example, to enhance compatibility with Magnetic Resonance Imaging (MRI) machines, it may be desirable to make system 10 in a manner that would impart a degree of MRI compatibility. For example, system 10 may be made of a material that does not substantially distort the image and create substantial artifacts (artifacts are gaps in the image). Certain ferromagnetic materials, for example, may not be suitable because they may create artifacts in an MRI image. System 10 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be utilized for one or more of the components of the system 10 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the polymer can contain up to about 6% LCP.

One or more of the components of system 10 may include a covering along the interior, exterior or both the interior and exterior surfaces thereof. The covering may be made from a polymer (including any of those listed above) or any other suitable material. In some embodiments, the covering may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or covering may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present disclosure.

It should be understood that this disclosure is, in many respects, only illustrative. Changes may be made in details, particularly in matters of shape, size, and arrangement of steps without exceeding the scope of the disclosure. The disclosure's scope is, of course, defined in the language in which the appended claims are expressed.

What is claimed is:

1. An embolic material delivery assembly, comprising:
   an outer member having a lumen extending therein and a distal end region;
   an inner member disposed within the lumen of the outer member, wherein the inner member includes two or more lumens extending therein;
   two or more embolic materials extending within the two or more lumens of the inner member, the two or more embolic materials each having a distal end region and a proximal end region; and
   an anchor disposed within the lumen of the outer member, the anchor having an attachment region;
   wherein the distal end region of each of the two or more embolic materials is coupled to the attachment region of the anchor when the anchor is disposed within the lumen of the outer member.

2. The assembly of claim 1, wherein the anchor is positioned distal to a distal end of the inner member.

3. The assembly of claim 1, wherein the anchor includes a coiled wire.

4. The assembly of claim 3, wherein coupling each of the two or more embolic materials to the attachment region of the anchor includes engaging the distal end region of each of the two or more embolic materials with at least one winding of the coiled wire.

5. The assembly of claim 4, wherein each of the two or more embolic materials defines a length extending between the distal end region and the proximal end region, and wherein the proximal end region of each of the two or more embolic materials is disposed within the inner member prior to deployment.

6. The assembly of claim 4, wherein the proximal end region of each of the two or more embolic materials extends proximally from the inner member catheter prior to deployment.

7. The assembly of claim 3, wherein the inner member is configured to translate along a longitudinal axis of the outer member, and wherein translation of the inner member pushes the coiled wire out of a distal end of the outer member.

8. The assembly of claim 1, wherein the anchor includes an elongated shaft member having a first arcuate portion and a second arcuate portion.

9. The assembly of claim 8, wherein the attachment region includes an aperture, and wherein coupling each of the two or more embolic materials to the attachment region of the anchor includes engaging the aperture.

10. An embolic material delivery assembly, comprising:
    an embolic coil having a proximal end and being disposed within a delivery catheter;
    an inner catheter including two or more lumens extending therein,
    the inner catheter being slideably disposed within an outer catheter and being proximal of the embolic coil;
    two or more embolic materials, each of the two or more embolic materials extending within a separate lumen of the two or more lumens of the inner catheter and having a distal end region; and
    wherein the outer catheter includes an aperture having a cutting edge and extending through a distal side wall of the outer catheter, and a distal end of the inner catheter is located proximal of the aperture in a first configuration,
    wherein the distal end region of each of the two or more embolic materials is coupled to the proximal end of the embolic coil at a point distal of the outer catheter,
    wherein in a second configuration the distal end of the inner catheter is located distal of the aperture through the distal side wall of the outer catheter and each of the two or more embolic materials has been severed by the cutting edge.

11. The assembly of claim 10, wherein the embolic coil is positioned distal of the outer catheter.

12. The assembly of claim 11, wherein the outer catheter is sized and configured to translate within a lumen of the delivery catheter, and wherein distal translation of the outer catheter pushes the embolic coil out of a distal end of the delivery catheter.

* * * * *